United States Patent [19]

Kennedy

[11] 4,354,156
[45] Oct. 12, 1982

[54] DEVICE FOR DETECTING FERROMAGNETIC MATERIALS

[75] Inventor: Stanley P. Kennedy, Newark, Del.
[73] Assignee: E. I. Du Pont de Nemours & Company, Wilmington, Del.
[21] Appl. No.: 146,778
[22] Filed: May 5, 1980

Related U.S. Application Data

[63] Continuation of Ser. No. 841,449, Oct. 12, 1977.

[51] Int. Cl.³ .............................................. G01N 27/72
[52] U.S. Cl. .................................. 324/228; 324/236; 324/239; 102/313
[58] Field of Search ............... 324/228, 234, 236, 239, 324/238; 340/506, 513

[56] References Cited

U.S. PATENT DOCUMENTS

| | | | |
|---|---|---|---|
| 1,708,524 | 4/1929 | Tatz . | |
| 2,434,347 | 10/1976 | Browne | 324/234 |
| 2,495,627 | 1/1950 | Bovey | 324/234 |
| 2,575,447 | 11/1951 | Gossick | 324/239 |
| 3,059,749 | 10/1962 | Zinke | 324/234 |
| 3,394,304 | 7/1968 | Green | 324/234 |
| 3,867,689 | 2/1975 | Mori | 324/234 |
| 3,986,430 | 10/1976 | Coursen | 102/21 |

OTHER PUBLICATIONS

J. Ryder, Electronic Fundamentals and Applications, (4th ed., Prentice-Hall, 1970) pp. 102–105.
W. Hayt et al., Engineering Circuit Analysis (2nd. ed., McGraw-Hill, 1971) p. 122.

Primary Examiner—Richard E. Schafer
Assistant Examiner—Edward F. Miles
Attorney, Agent, or Firm—Diamond C. Ascani

[57] ABSTRACT

Apparatus for detecting ferromagnetic material such as is present in an explosive cartridge being loaded into a borehole, e.g., according to the method described in U.S. Pat. No. 3,986,430, which includes an inductance coil connected in series with a resistor, separately rectifies and amplifies the AC voltages across the coil and resistor and connects them in series opposition. The value of the balancing resistance is adjusted so that the two rectified voltages are equal and opposite when no ferromagnetic material is present. When the unbalance voltage exceeds a threshold value, a signalling device is actuated.

6 Claims, 2 Drawing Figures

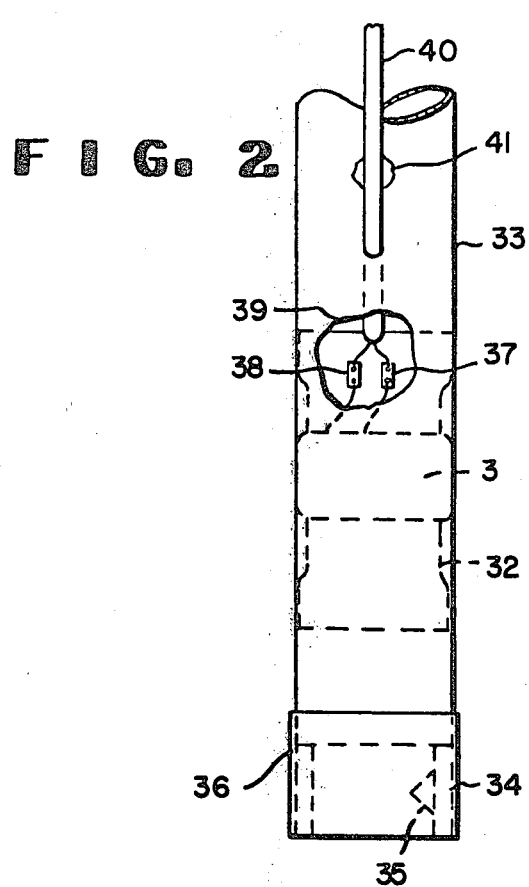

DEVICE FOR DETECTING FERROMAGNETIC MATERIALS

This is a continuation, of application Ser. No. 841,449, filed Oct. 12, 1977.

BACKGROUND OF THE INVENTION

1. Field of the Invention

The present invention relates to an apparatus for detecting ferromagnetic materials, and particularly to an apparatus for sensing the motion of ferromagnetic bodies for the purpose of counting them.

2. Description of the Prior Art

U.S. Pat. No. 3,986,430, issued Oct. 19, 1976, describes a method of loading explosive cartridges downwardly into a borehole wherein the descent of the cartridges is guided through a retractable flexible tubing assembly through which a stream of water flows. The cartridges preferably are cut open just before their discharge from the assembly, and their passage through, or discharge from, the assembly is indicated outside the borehole. The assembly is retracted incrementally until completion of the loading.

The feature of sensing and indicating the passage of the cartridges through, or their discharge from, the cartridge-guiding assembly is important inasmuch as it provides information on whether the cartridges fed into the tubing assembly are being discharged or whether the flow has ceased due to blockage, e.g., by the buildup of cartridges in the assembly. The loading method requires a device which is (a) capable of sensing the motion of the cartridges in the environment of the borehole, e.g., in water possibly contaminated with materials such as salts; (b) compact and sufficiently simple in design to allow it to be used in conjunction with the cartridge-guiding tubing without interfering with the motion of the cartridges therethrough, and with a minimum number of connections to the surface; and (c) cheap enough to be expended when the cartridges are subsequently detonated. In addition, it is desirable that the device be functional at great depths, e.g., at 1000 feet or deeper, and be able to detect small objects moving at high speed.

The requirements of the described cartridge loading method preclude the use of various of the counting techniques known in the art. For example, permanent magnetization of a metal clip which closes the end of a chub cartridge and detection of the presence of the clip by a Hall effect device are unsuitable because the device is too expensive to be expendable, and four lead wires are required between the sensor located in the loading assembly and the electronics box on the surface. The use of an inductance coil in the assembly to sense the presence of a steel cartridge clip is more suitable with respect to expendability, but presents certain other problems associated with the detection circuit. If a conventional alternating current bridge with resistances, a use of which is described in U.S. Pat. No. 1,708,524, is used, accurate counting is hampered by the fact that no true null occurs due to the large out-of-phase signal caused by a phase shift in the inductance and stray capacitances. An impedance bridge is costly as well as troublesome in that the balancing of variable lead wire impedances requires interactive resistance and reactance adjustments.

SUMMARY OF THE INVENTION

The present invention provides an apparatus for detecting ferromagnetic material, e.g., in an explosive cartridge being loaded into a borehole, comprising:
(a) a source of alternating current, e.g., an oscillator;
(b) an inductive sensing coil having a magnetic field, powered by the source of alternating current;
(c) a balancing impedance, e.g., a resistor, in series connection with the inductive sensing coil, the balancing impedance being adjusted in a manner such that the amplitude of the voltages across the inductive sensing coil and the balancing impedance are approximately equal in the absence of ferromagnetic material in the coil's magnetic field;
(d) first and second means for rectifying electrical signals, the first means rectifying a signal appearing across the inductive sensing coil, and the second means rectifying a signal appearing across the balancing impedance, the first and second rectifying means producing rectified signals of opposite polarity;
(e) summing means, e.g., summing resistors, joining the outputs of the first and second rectifying means, for producing an electrical signal proportional to the algebraic sum of the signals produced by the first and second rectifying means;
(f) means for sensing a change in the electrical signal produced by the summing means in response to the presence of ferromagnetic material in the coil's magnetic field; and
(g) means for indicating the sensed change in electrical signal.

BRIEF DESCRIPTION OF THE DRAWING

FIG. 2 is a schematic representation in elevation of a portion of an apparatus for loading explosive cartridges into a borehole wherein the passage of cartridges is sensed by the apparatus of this invention, the loading apparatus including a wire coil whose inductance is changed by the passage of cartridges therethrough.

DETAILED DESCRIPTION

Figure 1:
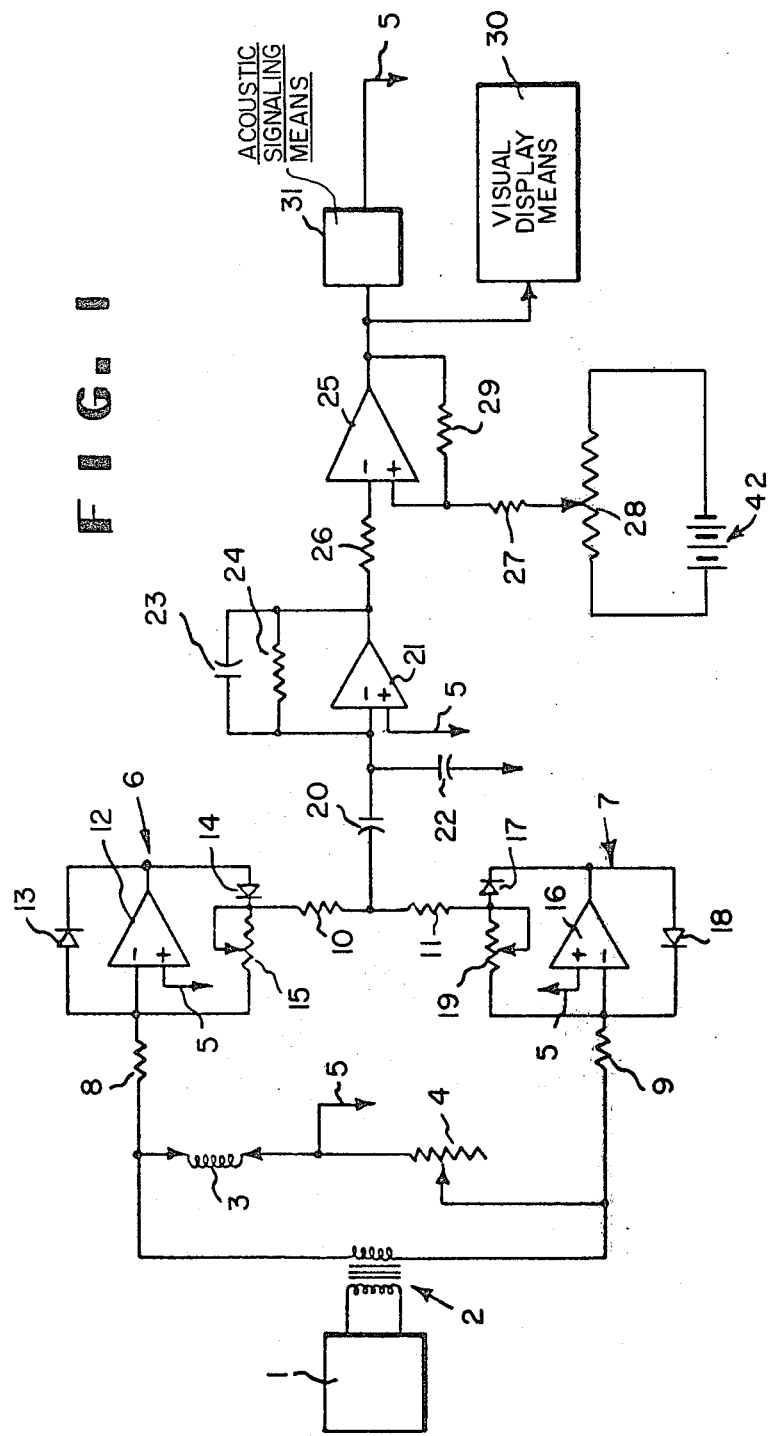
FIG. 1 is a diagram of an inductance-monitoring circuit of the invention.

In the present invention, the presence of ferromagnetic material is sensed by an inductance coil connected in series with a balancing impedance, e.g., a fixed or adjustable resistor, and excited by a source of alternating current, e.g., an oscillator. The inductance of the coil increases when ferromagnetic material is present in the coil's magnetic field, thereby increasing the AC voltage across the coil. The AC voltage across the coil and the balancing impedance are separately rectified, amplified, and connected in series opposition. The value of the balancing impedance is adjusted so that the two rectified voltages are equal and opposite when no ferromagnetic material is present. When the unbalance voltage exceeds a threshold value, a signalling device and, if desired, a counter are actuated.

The present apparatus offers several advantages for use in sensing the passage of explosive cartridges through the cartridge-guiding assembly in a borehole as described in the aforementioned U.S. Pat. No. 3,986,430, the disclosure of which is incorporated herein by reference. First, because voltages are rectified before being compared, the above-mentioned problem of phase shift in the inductance encountered with a conventional resistance bridge is avoided. Second, the coil can be excited at a frequency of about 1000 hertz so that eddy current losses in a conductive environment are acceptably small and the filtering of frequencies (60 hertz and its harmonics) originating in nearby power equipment is relatively easy. Third, balancing of the circuit with no ferromagnetic material in the coil permits convenient operation despite variable lead wire resistance and changes in coil resistance with temperature. No subsequent adjustment to compensate for system drift is required. Furthermore, the sensing coil is inexpensive enough to be expendable and small enough to be inserted in the cartridge-guiding tubing without obstructing the passage of the cartridges, yet is able to sense a ferromagnetic end-sealing clip on the cartridge while excluding non-ferromagnetic material, such as an aluminum clip on the opposite end of the cartridge. Finally, only two wires, a simple twisted pair, are required between the coil and the remainder of the apparatus located on the surface, in contrast to the requirements of the aforementioned Hall-effect device, for example.

The apparatus of the invention will now be illustrated with reference to FIG. 1 in which a source of alternating current 1, e.g., an oscillator, generates approximately three volts Peak to Peak a.c. at a frequency of one kilohertz. This furnishes power through coupling transformer 2 to the series combination of inductive sensing coil 3 and balancing impedance 4, in this case an adjustable resistor (typically adjusted to 200 ohms). The junction of coil 3 and resistor 4 is connected to the circuit common 5, which preferably is also the circuit ground.

The equal AC voltages referenced to circuit common 5 appearing across coil 3 and adjustable resistor 4 are applied to precision rectifier circuits 6 and 7 through resistors 8 and 9 (typically 470 ohms), respectively, with the outputs of the two rectifier circuits joined through summing resistors 10 and 11 (typically 5600 ohms).

Precision rectifier circuit 6 is composed of amplifier 12, diodes 13 and 14, and feedback resistor 15 (typically 1500 ohms) connected so as to linearize the rectifier characteristics of diodes 13 and 14, i.e., force the circuit to behave as an ideal rectifier element. Such a circuit is known in the art, and is more fully described in the *Handbook of Operational Amplifier Applications, Burr-Brown Research Corporation, Tucson, Ariz.*, Ed. 1, 1963, page 70. Similarly, precision rectifier circuit 7 is composed of amplifier 16, diodes 17 and 18, and feedback resistor 19, and is arranged to rectify the negative-going half-cycle of the applied voltage, with reference to circuit common 5, while circuit 6 rectifies the positive-going half-cycle.

The voltage at the junction of resistors 10 and 11 is coupled to amplifier 21 through coupling capacitor 20, whose value is so chosen that, in conjunction with the input resistance of amplifier 21, low-frequency voltages, including DC voltage, are not passed to the input of amplifier 21. Similarly, the value of capacitor 22 is chosen so that, in conjunction with resistors 10 and 11, the higher frequency voltages are shunted to circuit common, and not passed to amplifier 21. Thus the frequency response of amplifier 21 is determined by its input resistance, the source resistors 10 and 11, and capacitors 20 and 22. The amplifier 21 characteristics, e.g., gain and stability, are determined by feedback elements, resistor 24 (typically 2 meg ohms) and capacitor 23 (typically 0.01 mfd) in conjunction with capacitor 22.

The output of amplifier 21 is coupled through resistor 26 to a voltage level detector, consisting of amplifier 25 and resistors 27 and 29. The triggering threshold is determined by the voltage produced at the junction of resistor 27 and the arm of potentiometer 28, which is powered by DC voltage source 42, typically adjusted to 0.5 volt. The level detector circuit is essentially a biased amplifier, as is more fully described in the aforementioned handbook, page 46. The signal from amplifier 25 may be fed to a counter and visual display means 30 and also to an acoustic signalling means 31.

In FIG. 2, a 700-turn coil 3 of No. 34 copper wire is wound around the recessed portion of a spool-like, thin-walled plastic, hollow coil form 32. Coil 3 has an outer diameter of 1.75 inches (45.4 mm.), and a height of 0.75 inch (19 mm.). The inner diameter of coil form 32 at the recessed portion is sufficiently large to allow explosive cartridges to pass through, and the largest outer diameter of the coil form is 1.75 inches (45.4 mm.). Coil form 32 is held in position in tubing 33, as is described in the aforementioned U.S. Pat. No. 3,986,430. In the latter patent the tubing is denoted by the numeral 5 in FIG. 1 and FIG. 2. As is described therein, the coil form is held in position in the tubing by force fit about a foot (30.5 cm.) above an open-eyed cylindrical member, e.g., a short rigid nozzle, designated 34 herein. Cylindrical member 34 is located at the discharge end of a tubing assembly through which explosive cartridges are loaded into a borehole, and is joined to the tubing by tight taping 36. Cutting means 35 is mounted to the inner wall of cylindrical member 34 to cut the cartridges open just before their discharge from the assembly.

Metal tabs 37 and 38 are attached to the outer wall of coil form 32 by any suitable procedure. A temporary hole 39 in the wall of tubing 33 permits one end of the wire which forms coil 3 to be soldered to metal tab 37 and the other end to metal tab 38. One end of one of the two 24-gage copper wires in insulated duplex wire 40 is also soldered to metal tab 37, and one end of the other of the two wires to metal tab 38. Coil 3, tabs 37 and 38, and the exposed portions of the wires are protected with a coating of a water-proofing agent, and a patch is placed over hole 39. When the assembly is in position in a borehole, as is shown in FIG. 1 of U.S. Pat. No. 3,986,430, duplex wire 40, preferably affixed to the outer wall of tubing 33, e.g., by intermittent applications of hot-melt adhesive 41, extends to the surface where it is connected to the remainder of the circuit shown in FIG. 1 herein. One of the conductors of duplex wire 40 at the surface is connected to the junction of transformer 2 and resistor 8, and the other to adjustable resistor 4.

In operation, the circuit is adjusted to a balanced condition in the quiescent state, i.e., with no ferromagnetic material within coil 3. Adjustable resistor 4 is used to balance the circuit so that the amplitude of the voltage across coil 3 is equal to the amplitude of the voltage across resistor 4. Similarly, variable resistors 15 and 19 are adjusted to provide equality in the precision rectifier circuits, as denoted by zero voltage from the junction of resistors 10 and 11 relative to the circuit common 5. Also, resistors 15 and 19 are further adjusted to provide maximum attainable amplification in rectifiers 6 and 7, respectively, limited only by amplifier saturation and the above-mentioned equality requirement.

The explosive cartridge whose passage is to be detected contains a material having high magnetic permeability. For example, the ends of a chub cartridge (a tube of plastic film, filled with explosive, and gathered at both ends and closed, e.g., by means of closure bands) are closed with an iron clip at one end and an aluminum clip at the other so that only one signal is obtained from each cartridge. When such a cartridge passes through coil 3, the latter's inductance and impedance increase because of the presence of the ferromagnetic material (iron) within its field of influence, thus increasing the voltage drop across coil 3. This causes an imbalance in the circuit such that the positive rectified voltage no longer is equal to the negative rectified voltage, and the difference appears at the junction of resistors 10 and 11, with relation to circuit common 5. This transient difference voltage, after filtering, is amplified in amplifier 21 (which is the means of sensing the change in the electrical signal produced by the summing means), and in turn actuates the voltage level detector, thus providing a signal which is fed to counter and visual display means 30 and to acoustic signalling means 31.

The proper operation of the apparatus described above requires the selection of the proper values of the filtering capacitors 20 and 22. The shunting capacitor 22, which essentially determines the high-frequency cut-off of which is effectively a band-pass filter, serves to eliminate voltages of the applied power frequency, and higher. Additional capacitance, i.e., lowering the cut-off frequency, serves to discriminate between a cartridge having a ferromagnetic end clip and a possibly free-falling ferromagnetic clip. In this case, the rapid traverse of the coil by the clip would result in a rapid change of the balance voltage, which would be filtered out by shunt capacitor 22, while the traverse of the coil by a slower-moving cartridge would cause a lower rate of change of balance voltage, thus actuating the counter. The value of coupling capacitor 20 is equally important at the low-frequency cut-off end of the effective band-pass filter. This capacitor eliminates DC coupling to the amplifier, as well as changes in the balance voltage occurring over a relatively long period of time. Thus, changes in the balance condition occurring because of temperature drift in components, or use of the device in an environment containing magnetic material, e.g., in a borehole in rock containing magnetic material, such as iron ore, will not be transmitted through the capacitor causing false counts or amplifier saturation.

Thus, by selecting the proper values of the cut-off frequencies, as determined by the capacitors, the rate of change of unbalance effecting a count may be preselected. This, then, eliminates false counts caused by electrical noise, harmonics in the voltage supply, and also eliminates false counts caused by slowly occurring component drifts.

Although the described filtering means consisting of series- and shunt-connected capacitors, is particularly effective in the described cartridge-detecting apparatus, it will be understood that more sophisticated band-pass filters, giving sharper cut-offs, may be used.

When the apparatus of this invention is employed in the borehole loading method described in U.S. Pat. No. 3,986,430, a typical velocity of the cartridges through the tubing is in the order of 24 to 120 inches per second. With a coil having an effective magnetic length of 2.4 inches (coil length plus magnetic field extension beyond the ends of the coil), the time required for an iron clip on a chub cartridge to traverse the coil is 20–100 milliseconds. Thus, the shunt capacitor 22 must allow a voltage change taking place in 20–100 milliseconds to actuate amplifier 21, but power-supply ripple voltages, occurring in 1 millisecond or less, must be eliminated. A capacitor valued at 200 mfd will accomplish this. Similarly, slow changes, occurring in periods of 1000 milliseconds or more, are prevented from actuating amplifier 21 by selection of the value of the series coupling capacitor 20, typically, 25 mfd.

Other uses for the apparatus of the invention include the detection of ferromagnetic particles suspended in a fluid, and the detection of ferromagnetic material in the presence of conductive material, e.g., fluids of high conductivity and non-ferrous materials, which would falsely trigger sensing devices using radio-frequency detection methods.

I claim:

1. Apparatus for detecting small rapidly moving ferromagnetic objects comprising:
   (a) a source of alternating current;
   (b) an inductive sensing coil having a magnetic field, powered by said source of alternating current;
   (c) a balancing impedance in series connection with said inductive sensing coil, said balancing impedance being adjusted in a manner such that voltage amplitudes across said inductive sensing coil and said balancing impedance are approximately equal in the absence of ferromagnetic material in said coil's magnetic field;
   (d) first and second means for rectifying electrical signals, said first means half-wave rectifying a signal appearing across said inductive sensing coil, and said second means half-wave rectifying a signal appearing across said balancing impedance, said first and second rectifying means simultaneously producing half-wave rectified signals of oppposite polarity.
   (e) summing means joining the simultaneous outputs of said first and second rectifying means and producing an electrical signal proportional to the algebraic sum of the signals produced by said first and second rectifying means;
   (f) means for sensing a rapidly repetitive change in the electrical signal produced by said summing means in response exclusively to the rapid passage of ferromagnetic objects in succession through said coil's magnetic field;
   (g) a band-pass filter for blocking DC voltage interposed between the junction of said summing means and said means for sensing a change in the electrical signal produced by said summing means; and
   (h) means for indicating the sensed change in said electrical signal whereby the number of said objects may be counted.

2. Apparatus of claim 1 wherein said balancing impedance is an adjustable resistor.

3. Apparatus of claim 2 wherein said rectifying means are precision rectifier circuits and said summing means are summing resistors.

4. Apparatus of claim 3 including a voltage level detector driven by the filtered signal amplified by said change-sensing means.

5. Apparatus of claim 1 wherein said ferromagnetic objects are metal end closures on chub cartridges being loaded into a borehole at a rapid rate.

6. Apparatus of claim 5 wherein each of said chub cartridges has one metal end closure which is ferromagnetic and another which is nonferromagnetic, only the passage of the ferromagnetic end closure through said coil's magnetic field causing a change in the electrical signal produced by said summing means, whereby the number of said cartridges may be counted.

* * * * *